United States Patent [19]

Lee, Jr. et al.

[11] 4,150,485

[45] Apr. 24, 1979

[54] LIQUID PAINT-ON DENTAL RESTORATIVE PROCESS AND COMPOSITION

[76] Inventors: Henry L. Lee, Jr., 3534 E. California Blvd., Pasadena, Calif. 91107; Jan A. Orlowski, 1304 Rubio Dr., Altadena, Calif. 91001; Patrick D. Kidd, 415 N. Lina St., Sierra Madre, Calif. 91024

[21] Appl. No.: 832,927

[22] Filed: Sep. 13, 1977

[51] Int. Cl.$^2$ .............................................. A61K 5/00
[52] U.S. Cl. ................................. 32/15; 252/301.6 R; 252/301.6 S; 260/42.15; 260/42.28; 260/42.29; 260/42.52; 260/998.11
[58] Field of Search ............. 260/998.11, 42.52, 42.28, 260/42.29; 32/15; 252/301.6 R, 301.6 S

[56] References Cited

U.S. PATENT DOCUMENTS

| | | | |
|---|---|---|---|
| 3,452,437 | 7/1969 | Chang | 32/15 |
| 3,539,526 | 11/1970 | Bowen | 106/3 S |
| 3,539,533 | 11/1970 | Lee et al. | 260/47 |
| 3,751,399 | 8/1973 | Lee et al. | 260/47 UA |
| 3,792,531 | 2/1974 | Rossi | 32/15 |
| 3,975,203 | 8/1976 | Dietz | 106/299 |

*Primary Examiner*—James H. Derrington

[57] ABSTRACT

Low viscosity dental restorative coating compositions for application to natural and to artificial teeth, useful in covering surface imperfections including stains, gumline erosion, small pits, and the like. They are designed to impart to restored teeth the overall appearance of original teeth, particularly with respect to natural vitality and fluorescense, while effectively masking stains and themselves resisting discoloration from staining agents and upon aging. They are formulated to bond well, look natural, and wear well. As ready to use, a coating composition will contain from about 30% to about 70% filler by weight of the composition, in a resinous, curable liquid vehicle. The composition is formulated to be sufficiently fluid so that it can be applied to a dental surface easily and conveniently, as by brushing on a previous prepared surface, and it will flow to a featheredge. The composition nevertheless must be sufficiently viscous that dripping from the applicator, generally a brush, and dripping from the coated surface, are essentially absent. The filler is a blend of glass or silica and a fluorescent pigment. Also used are inhibitors, curing agents including peroxide catalysts and accelerators, dyes, ultraviolet absorber materials, and additives that retard settling.

12 Claims, No Drawings

LIQUID PAINT-ON DENTAL RESTORATIVE PROCESS AND COMPOSITION

FIELD OF THE INVENTION

This invention relates to flowable, paint-on dental restorative compositions and methods of using them to replace enamel and to repair defects, including covering permanent discolorations such as tetracycline stains, nicotine stains, and the like. These compositions are also capable of restoring porcelain and acrylic veneers in situ. These compositions are of the type that are conventionally packaged in two or more separate portions, each of which is individually shelf-stable, but which are mixed for use, to form a paintable composition that cures rapidly to form a hard coating.

DESCRIPTION OF THE PRIOR ART

An enamel coating or enamel replacement composition known to applicants is disclosed in a copending patent application, over which the present invention is an improvement. That copending patent application is Ser. No. 751,517, filed Dec. 16, 1976 now U.S. Pat. No. 4,107,845, entitled Dental Adhesive Composites, which is a continuation of an earlier patent application, Ser. No. 424,223, filed Dec. 13, 1973, now abandoned, which in turn is a continuation of a still earlier patent application, now abandoned, Ser. No. 215,112, filed Jan. 3, 1972 now abandoned.

In the copending patent application, Ser. No. 751,517 now U.S. Pat. No. 4,107,845, composite enamel coating compositions are described. A representative composition as disclosed therein is a flowable suspension that can be easily brushed or flowed on a tooth surface, consisting essentially of from 40% to 70% filler fibers by weight of the composite in a liquid acrylate or substituted acrylate resin binder having a viscosity of less that 5,000 centipoises. The fibers are from 1 to 100 microns in length and have diameters of from 1/20 to 1/5 of their lengths, respectively. The composition may include a peroxide initiator, an activator, and cosmetic ingredients such as, for example, dyes and pigments.

These enamel coating composites were designed to gel and to cure rapidly upon mixing and application to a tooth surface. These composites are essentially adhesive materials that the dentist can paint onto eroded or stained areas to restore them. They have the advantage that the work can be done in one visit in a few minutes, without drilling and without the use of an anesthetic. Older methods of treatment often required extensive drilling, the use of anesthetic, and often the costly fabrication of caps.

The compositions of the pending application generally are made available in the form of two separately packaged portions, to be mixed at the time of use. Each portion is shelf-stable in its own package, but upon mixing, the sequence of gelling, setting, and curing is initiated. Such a composition, when mixed and ready for application, generally is a semi-opaque paint-on coating. It can be mixed to various tooth shades and takes an excellent finish polish. It offers mechanical, chemical, biological and thermal protection to the tooth on which it is coated. It has been reported to provide immediate relief from food and temperature sensitivity and complete elimination of the sensitivity within a few weeks. The major intended use is to restore areas of erosion and to coat porous, soft or otherwise deficient enamel.

These coating compositions are also useful for cosmetic purposes, including, for example, for coating tetracycline stains and hypoplasia, for coating previously installed but worn or discolored composite restorations, and for restoring small Class I and III cavities primarily in enamel.

These coating compositions were and are good products for their intended purpose. Experience in use has demonstrated, however, certain areas where improvements are possible, particularly with respect to more closely approaching the appearance of natural teeth, especially their natural vitality and fluorescence. Such esthetic characteristics are particularly important when restored teeth are viewed under visible light rich in short wave lengths. Under these conditions, the coatings produced in accordance with that earlier invention appear dark. Moreover, experience with coatings produced from those compositions has indicated that they tend to discolor upon prolonged and repeated exposure to such staining agents as coffee, tea, and nicotine, and that they tend to discolor upon aging, necessitating visits back to the dentist for recoating or replacement.

The compositions of the pending application, and those of the present application also, are to be distinguished from fissure and margin sealers that are useful for filling and sealing natural pits and fissures and the gaps that may develop around amalgam fillings.

Fissure sealants are designed to fill natural pits, fissures, and cracks in the enamel, to seal the enamel and dentin and to protect them. Margin sealants are basically intended to penetrate and fill any crevices or gaps at the margins between dental restorative filling material and the tooth structure about a cavity. They prevent loosening of fillings and penetration of food and bacteria. Pits, fissures, and cracks in the enamel, and open margins as well, can be the locus of new caries formation.

Sealant compositions of this kind are often used on molars, where their functional characteristics are important and their appearance is either of little concern or not of great importance. Moreover, sealants, because they have to penetrate narrow crevices, fissures and cracks, have too low viscosity to be applied as a coating restorative. One example of a dental sealant composition may be found in the formulations described in U.S. Pat. No. 4,001,483, granted Jan. 4, 1977, to Henry L. Lee, Jr. and Jan A. Orlowski. Such sealant compositions are intended for a highly specialized purpose and fill a different need from that to which the coating compositions of either the pending application or the present application are directed.

Fissure and margin sealant compositions have been designed primarily for functional purposes, generally without regard for cosmetic considerations. Consequently, the compositions of the pending application mentioned above, and of the present invention as well, are useful for painting over coatings of such sealant compositions, to improve their appearance.

To be fully satisfactory, enamel coatings must not only mask stains, avoid discoloration themselves, seal against the entry of food particles, moisture, and microorganisms, and act as thermal insulators, they must also bond well, wear well, and look good. Some prior art dental compositions fulfilled some of these requisites, but not all, and except for the enamel coatings of the copending application, none were designed for or suitable for use as enamel coatings. Thus, U.S. Pat. No. 3,452,437 describes direct dental filling compositions, i.e., thick paste products, that include a finely divided filler that may contain a minute amount, 0.28% by weight of the composition, of a fluorescent pigment. Direct dental filling compositions are not useful as paint-on enamel coatings, and require entirely different properties both before use and after installation. Such compositions are generally used by trowelling an amount of the paste into position in a cavity, tamping the paste down to insure complete contact, then carving the increasingly stiff curing paste into at least a rough outline of the desired shape. Final shaping and polishing is done with a drill. Such compositions are not useful as paint-on enamel coatings and are formulated with much different objectives than enamel coating.

Similarly, U.S. Pat. No. 3,539,526 also describes direct dental filling compositions, that in this case include a multi-component inorganic filler made of a mixture of fused silica particles, barium-containing glass, amber or other colored glass for color matching, and optionally, up to 1% of a fluorescent pigment. U.S. Pat. No. 3,962,267 describes dental cements that may include the same fluorescent pigment.

Lee et al, U.S. Pat. No. 3,539,533, and Lee and Stoffey, U.S. Pat. No. 3,751,399, describe resin binder systems that may be used in various dental restorative applications, as do also Lee and Stoffey, U.S. Pat. No. 3,769,336, Lee et al., U.S. Pat. No. 3,770,811, and Lee et al, U.S. Pat. No. 3,815,239. None of these, however, disclose or suggest liquid dental restorative compositions for painting on to replace or repair enamel, nor particularly, compositions such as those of the present invention.

SUMMARY OF THE INVENTION

The present invention provides paint-on adhesive dental restorative compositions that can be painted or brushed onto a previously prepared surface of a tooth or of a porcelain or acrylic crown. Best results are obtained when enamel areas have been previously prepared by cleaning and mild etching. Usually a primer, to improve bonding, is helpful in connection with restoring an acrylic or porcelain surface.

These compositions are formulated for the correction of abnormalities in the enamel, which is a major dental problem. They are particularly designed to be coated on previously prepared enamel, and serve preventive, restorative, and cosmetic functions. The use of such an enamel coating eliminates the need to prepare the tooth for a cap.

Such a dental coating composition can be formulated to match the appearance of the surface on which it is placed and of adjacent teeth, and to match and retain its appearance in all kinds of light, including ultraviolet light. Moreover, a coating applied from a composition made in accordance with a preferred embodiment of the invention imparts excellent vitality and not only has an excellent cosmetic appearance, but also will not appear to be dark, nor discolor, under ultraviolet light.

A composition, as mixed and ready for application in accordance with the present invention, is a flowable material that can be easily painted on. It consists essentially of a resinous, curable liquid, filler material, thickener, initiator and activator, ultraviolet absorber, and appropriate dyes, stabilizers, and other such materials. The curable liquid is a liquid acrylate or substituted acrylate that has a low viscosity. After admixture with the filler and other ingredients, the composition is readily painted on as a fluid or flowable material. The binder may be cross-linkable or not, depending upon the acrylate system employed.

The filler is a mixture of finely divided particulate inorganic materials, including 80% or more of the filler of conventional filler materials, together with 20% or less of a finely divided fluorescent material. One preferred filler material is a barium borosilicate glass. The equivalent spherical diameter of the filler mixture is in the range of from 0.2 to 20 microns, preferably about 2 microns. The filler mixture ordinarily forms from 30% to 70% by weight of the total composition, with the curable liquid and the other ingredients forming the balance. The filler mixture ordinarily constitutes a relatively small percentage by volume of the total composition, below 50% and usually on the order of 25% to 30% or less. The amount of a filler is carefully balanced so that the filled composition retains flowability for ease in brushing or flowing onto the enamel or other surface by any convenient technique. One useful additive comprises super fine silica, that serves to reduce or eliminate sedimentation, and to keep the applied coating in its intended location while it gels and then sets.

The catalyst and activator perform their normal functions. The use of an ultraviolet absorber is particularly important in the compositions of this invention to prevent discoloration of the binder after exposure to light.

Properly formulated, in accordance with preferred embodiments of the invention, enamel coatings of controlled opacity are obtained that are wear resistant and that resist discoloration on aging, and resist staining even upon prolonged and repeated exposure to common staining agents. Such coatings are useful as protective coatings and for beautifying dental surfaces.

DETAILED DESCRIPTION OF THE INVENTION

The compositions of the present invention must meet very demanding tests, to be satisfactory. They must bond well to tooth surfaces. After cure, they must have a natural look. Furthermore, after months and years in the oral environment, during which time they are subjected to the abrasion that comes from brushings and to exposure to food, light and bacteria, they must retain their good appearance, should not crack or break, and should exhibit minimal if any erosion.

A suitable composition in accordance with the present invention, when ready for application to a previously prepared tooth surface, consists of a curable liquid; finely divided solid components, including a particulate filler; curing agents, including an initiator and an activator; a color stabilized against being an absorber of ultraviolet light; dyes that impart a particular color or shade; and other additives as considered necessary or desirable.

The curable liquid will have a viscosity of less than about 5,000 centipoises at 25° C. as measured on a Brookfield viscometer, model RBT, spindle spindle number 5, operated at 20 rpm. The curable liquid is an ester of acrylic or alkyl substituted acrylic acid that is selected from the group consisting of (i), a blend comprising from 20% to not more than 90% by weight of an aromatic or cycloaliphatic diacrylate or dimethacrylate, and at least 10% by weight of an aliphatic tri-, di- or mono-acrylate or methacrylate; (ii), a homopolymerizable hydrogenated aromatic diacrylate or dimethacrylate; and (iii), mixtures thereof wherein the total amount of aromatic or cycloaliphatic diacrylate or dimethacrylate does not exceed 90% of the curable liquid.

The other major constituent of the composition is a finely divided, particulate filler mixture that forms from 30% to 70% by weight of the composition, but less than 50%, and usually on the order of 25% to 30% or less, of the composition by volume, so as not to impair its paintability. Of this filler component, at least 1% and not more than 20% by weight is a fluorescent pigment material, preferably a zinc-magnesium oxide complex. The balance is a finely divided filler material of a conventional kind that is not fluorescent, preferably a barium borosilicate glass filler. The particle equivalent spherical diameter of the filler is up to 20 microns, preferably about 2 microns.

The minor ingredients of the composition include: curing agents, preferably a peroxide-type initiator; a tertiary aromatic amine activator; an ultraviolet absorber; and suitable dyes.

As those skilled in the art will understand readily, the curable liquid may be formed from a blend of several different but compatible materials. Similarly, the filler mixture may contain small amounts of specific filler-type additives to enhance polishability, to adjust opacity, to prevent sedimentation, and for other purposes.

The preferred kind of packaging is a kit that includes a curable liquid resin component, a powder filler component, particulate opaquing agent, dyes for color matching, a measuring device, and one or more applicators. The curable liquid preferably is packaged in two or more shades in different containers, for ease in color matching.

The Curable Liquid

The curable liquid has a viscosity of 5,000 centipoises or less at 25° C. It may be a blend of an aromatic or hydrogenated aromatic diacrylate or dimethacrylate with an aliphatic di- or mono-acrylate or methacrylate in a weight ratio of not more than 90% of the former to 10% of the latter. The curable liquid may also be formed from a homopolymerizable hydrogenated aromatic diacrylate or dimethacrylate, or their blends with the polymerizable materials cited above.

It is of course possible to use more than one aromatic or hydrogenated aromatic diacrylate or dimethacrylate, and to dilute this material with one or more different aliphatic di- or mono-acrylates or methacrylates. In particular, in a curable liquid blend, the aliphatic diacrylate or dimethacrylate used as the cross-linking agent in the blend is preferably a diethylene glycol or triethylene glycol diacrylate or dimethacrylate.

When the curable liquid includes an aromatic diacrylate or dimethacrylate, it should contain at least two aromatic rings in its structure. A preferred example of such a diaromatic diacrylate is 2,2-bis[4'-(3"methacryloyl-2"-hydroxy propoxy)-phenyl]-propane, known as bis/GMA.

When the curable liquid includes a hydrogenated aromatic diacrylate or dimethacrylate, a preferred material is (methacryloyl-2-hydroxy propoxy)-(methacryloyl ethyl-tetrahydro phthalate). One way of making such mixed adducts is described in the copending application of Lee, Ser. No. 768,765, filed Feb. 15, 1977 now U.S. Pat. No. 4,102,856.

When a blend form of curable liquid is employed, particularly useful blends may be formed from diacrylates and dimethacrylates of the kind disclosed, for example, in U.S. Pat. No. 3,751,399, granted Aug. 7, 1973, to Henry L. Lee, Jr. and Donald G. Stoffey.

The Filler

The filler to be utilized is a blend of at least two filler materials, i.e. one part that imparts strength and hardness, and one that imparts the desired fluorescence.

The first filler material, which itself may be a mixture, is a conventional kind of filler such as, for example, silica (preferably of the amorphous type), quartz, or glass, or a mixture of these. A preferred kind of glass filler is a barium borosilicate glass, particularly barium boroalumino silicate. The second material or component of the filler is an inorganic fluorescent material, preferably a fluorescent zinc-magnesium oxide pigment. The particle size range of the filler material should preferably be from 0.1 microns to 30 microns and the equivalent spherical diameter should be 0.2 to 20 microns, preferably about 2 microns.

The fluorescent portion of the filler must be present in an amount of at least 1% by weight of the total amount of filler, and not more than 20% by weight of the filler, with a preferred range of from 4% to 7% by weight. A preferred material is the zinc-magnesium oxide complex sold under the trademark "OTTALUME 2115" by Ferro Corporation.

Fluorescent pigments have the unusual property of absorbing light at higher frequencies and re-emitting the absorbed energy at lower frequencies (longer wave lengths). The intensity of the fluorescence from any particular material is proportional to the concentration and activity of the fluorescent substance contained in that material. However when a fluorescent constituent is present at a high concentration, a decrease in mechanical properties, in addition to excessive opacity, is observed.

The preferred fluorescent pigments, for use in connection with the present invention, are those prepared in accordance with U.S. Pat. No. 2,481,344, having the composition range described in that patent. The optimum composition is about 88% zinc oxide and about 12% magnesium oxide, activated by the presence of a small amount of lithium sulphate. The amount of lithium sulphate present depends upon the processing technique employed, and may be as little as 0.25% based on the total pigment weight or as much as 5% of the total pigment weight. Other inorganic fluorescent pigment materials, having substantially the same fluorescent activity as the optimum products described in that patent (that is, for example, the commercially available product sold under the trademark Ottalume 2115) can be used in the practice of the present invention.

Best results are obtained when all of the inorganic filler particles are treated with a keying agent to improve the bond between the curable liquid and the surfaces of the finely divided filler particles. Keying agents that have been found to be suitable include the ethylenically unsaturated organosilane finishing or keying agents. A particularly useful keying agent is gamma-methacryloxypropyltrimethoxysilane. The amount employed may be enough to deposit about ½ of 1% of the silane on the particles, by weight of the filler particles. The finely divided filler particles may also be treated with a keying agent as described in the copending U.S. patent application Ser. No. 662,226 of Lee, Stoffey and Orlowski, filed Feb. 27, 1976, which is a continuation of another patent application, Ser. No. 436,685, filed Jan. 25, 1974 now U.S. Pat. No. 3,871,158, which in turn was a continuation of Ser. No. 146,465 filed May 24, 1971, now abandoned.

Desirable filler component materials, for the filler portion that is not fluorescent, are those which have been pretreated in accordance with the procedure described in copending application Ser. No. 401,808, of Lee and Orlowski, filed Sept. 28, 1973, i.e., the particles are treated with excess aqueous strong mineral acid at a temperature of at least 30° C. for at least one hour, then heated to 900° C. to 1200° C. to remove acid-insoluble materials.

Preferred filler components, for the non-fluorescent portion of the filler, are the materials that are disclosed in U.S. Pat. No. 3,826,788 granted July 30, 1974. These generally can be characterized as barium aluminosilicate glasses.

While the filler component forms from 30% to 70% of the coating composition by weight, the filler materials used, particularly in the preferred embodiments of the invention, are dense relative to the curable liquid. Consequently, the filler represents a smaller proportion of the coating composition by volume, with the result that the coating composition remains sufficiently fluid that it can be applied to a tooth surface and will flow readily to a featheredge, but that is sufficiently thixotropic that dripping is essentially absent.

Other Components

The curable liquid may be cured by admixture with curing agents such as an activator and an initiator. These components, and their concentrations, should be such that upon application to a tooth surface, the composition will cure relatively fast. A room temperature set in about ½ minute to about 10 minutes is desirable and preferably the coating should harden within about 2 minutes.

The amount of initiator and activator employed depends primarily upon the chemical composition of the liquid component and the working time that is desired.

Initiator is ordinarily employed in amounts in the range from about 0.2% to about 5% by weight of the monomer present in the curable liquid. Generally, an amount in the range from about 0.25% to 2.5% by weight of the monomer is satisfactory. Peroxide initiators are preferred, and are ordinarily employed in an amount in the range from about 1% to about 2% by weight, based on the weight of the monomer or monomers. While peroxide initiators such as benzoyl peroxide are preferred, other initiators are well known in the art and may be employed.

Generally the activator can be employed in an amount from about 0.001% to about 5% by weight of the monomers in the liquid. In most cases, the amount of activator will fall in the range from about 0.5% to about 2% by weight of the monomers in the liquid; usually, from about 0.5% to 1% by weight is sufficient. Examples of activators that may be used are dimethylparatoluidine and N,N-3,5-tetramethylaniline, and other aromatic tertiary amines that are well known in the art. A particularly preferred activator is N,N bis-(2-hydroxyethyl)-para-toluidine.

For best results, the coating compositions of this invention are stabilized by the incorporation in the composition of an ultraviolet absorber, which is generally incorporated in the resin. The ultraviolet absorber materials are energy degraders such as the substituted benzophenones. Discoloration of a coating may occur in the absence of such a stabilizer or absorber, particularly after exposure to ultraviolet light. One preferred ultraviolet absorber is 2-hydroxy-4-methoxybenzophenone, which is sold by the American Cyanamid Company under the trademark, Cyasorb UV9. Cyasorb UV9 and related materials are believed to operate by absorbing ultraviolet light preferentially, thus sparing the resin from its deleterious effect. Optimum optical properties of the material are obtained when the fluorescent pigment and ultraviolet absorber are present in balanced concentrations.

It is advantageous that the coating composition include an additive that functions as a thickening agent. The purpose of the thickening agent is to stabilize the coating composition against sedimentation and against flow after it has been applied to the tooth surface.

The viscosity of the coating composition must be controlled so that it flows well. A properly prepared tooth surface, that has been etched, for example, with 25% to 60% phosphoric acid for about 2 minutes, will tend to be rough. A sufficiently fluid composition will flow into crevices in the tooth surface and will form tag-like projections many microns in length, that help anchor the cured coating in place.

The coating composition must also be sufficiently fluid so that it is easily applied to the tooth surface with a brush, with a spatula, or with any other convenient applicator, to form a thin coating. To stabilize the coating against excessive flow or sag before the material gels and sets, a small but effective amount of the thickening agent, generally not exceeding 10% by weight of the filler, may be included in the composition. A preferred thickening agent additive is silica of sub-micron size, preferably of colloidal particle size. A suitable size range is from about 2 millimicrons to about 50 millimicrons, and preferably, from 4 to 20 millimicrons. The commercial silica products, Cabosil and Aerosil, are satisfactory materials.

Packaging

Preferably, this kind of dental coating composition is divided in two or more portions, formulated to be shelf stable, and packaged separately. These separate portions are then mixed in appropriate amounts, for application. The preferred formulation results in two portions, a liquid portion and a powder portion. The filler material, which preferably is conditioned with a silane or other keying agent, is ordinarily packed along with the peroxide catalyst as the powder portion. The liquid portion ordinarily contains the dyes required to produce the desired shade, and thus several packages of liquid may be included in a single kit, to permit a selection from among several shades.

Another useful form of packaging has the components divided into four portions, two of liquid and two of powder, respectively. One of the liquid portion packages and one of the powder portion packages can be mixed together to form a "Part A" paste, while the other liquid and powder portion packages respectively can be mixed together to form a "Part B" paste (as in Example 1 hereafter). These two pastes are then mixed together to form a coating composition in accordance with the invention. The Part A liquid portion and the Part B liquid portion may be very similar, in that each may contain a quantity of polymerizable liquid admixed with the ultraviolet light absorber material and, optionally, a small amount of filler. One of the packages of liquid, such as the Part B package, should contain the activator as well. The Part A and Part B packages of powdered components are similar in composition, in that an important constituent of each ordinarily will be inorganic filler in finely divided form, such as, for example, amorphous silica that has been treated with a keying agent, mixed with the particles of fluorescent pigment, preferably activated zinc-magnesium oxide. One of the fillers, such as Part A package, should contain a polymerization initiator as well. The Part B liquid may consist of several separate packages, each of which contains the necessary amount of the different shades, such as, for example, light, universal, yellow, brown, and gray.

In the preferred form of packaging, where there are only two separately packaged portions to be mixed, the two portions may be in the preferred liquid-powder form, respectively, or they may both be pastes, or one may be a paste and the other a liquid.

Generally, shelf stability is obtained by separate packaging of the catalyst and the accelerator. Thus, in the two portion, liquid-powder form, the initiator may be incorporated in the powder, and the activator in the liquid.

Coatings prepared by mixing the separately packaged portions, in accordance with the present invention, exhibit outstanding wear resistance, compression strength up to 44,000 psi, high hardness (up to 114 Rockwell H), good color stability, natural fluorescence in all types of light, including sunlight, artificial light, and near ultraviolet light, natural translucency, good adhesion to etched enamel and roughened porcelain, and an appearance of natural vitality with $C_{70}$ values in the range from about 0.60 to about 0.80. Coating compositions prepared in accordance with the present invention are compatible with dental bases and liners that are often used in conjunction with filling composites, or with the primers used for enhancing adhesion to gold or to dentin.

The invention may be further exemplified by several specific demonstrations thereof that appear in the following examples. In this application, all parts and percentages are by weight unless otherwise specified, and all temperatures are on the Celsius scale unless otherwise specified.

EXAMPLE 1

Four Portion Packaging

This example demonstrates one preferred embodiment of the new fluorescent paint-on coating compositions. The composition of each separately packaged portion is as follows:

| Part A |  |
|---|---|
| Liquid Portion | Parts by Weight |
| 1. (3-methacroyl-2-hydroxypropyl)-(2-methacroyl-ethyl)-tetrahydrophthalate - monomer | 100.0 |
| 2. Cyasorb UV9 - ultraviolet light absorber | 0.6 |
| 3. Aerosil consistency modifier | 3.0 |
| 4. 4-tert-butyl-2-hydroxy-toluene - inhibitor | 0.12 |
| Powder Portion | Parts by Weight |
| 1. amorphous silica, treated with silane keying agent and containing 1% by weight of benzoyl peroxide - filler | 100.0 |
| 2. Ottalume 2115 (magnesium oxide-zinc oxide complex) - fluorescent agent | 5.0 |
| 3. Cab-O-Sil - consistency modifier | 3.5 |

As the initial step in preparing a coating composition for use, appropriate amounts of these two portions are mixed together to form a readily flowable suspension in the ratio of 1.2 parts of powder to 1 part of the liquid.

| Part B |  |
|---|---|
| Liquid Portion | Parts by Weight |
| 1. blend of 60% bis/GMA with 40% triethylene glycol dimethacrylate- monomer | 100.0 |
| 2. Cyasorb UV9 | 0.4 |
| 3. N,N-bis(2-hydroxy-ethyl)-p-toluidine - activator | 2.0 |
| 4. Aerosil - consistency modifier | 3.0 |
| Powder Portion | Parts by Weight |
| 1. amorphous silica, treated with silane keying agent and containing plus 1% by weight of benzoyl peroxide - filler | 100.0 |
| 2. Ottalume 2115 fluorescent agent | 5.0 |
| 3. Cab-O-Sil | 5.0 |

As the second step in preparing a coating composition for use, appropriate amounts of these two Part B portions are mixed together to form a readily flowable suspension in the ratio of 1.7 parts of powder to 1 part of the liquid binder.

The necessary amounts of dyes are included in or may be added to prepare a desired shade of coating.

To prepare a coating composition for application to a previously prepared tooth surface, amounts of the Part A mixture and the Part B mixture are blended, in equal proportions. With a coating composition prepared in this manner, the following results were observed:

| Sample No. | Gel Time in Seconds at 22.5° C. | Set Time in Seconds at 22.5° C. |
|---|---|---|
| 1 | 92 | 188 |
| 2 | 97 | 181 |
| 3 | 90 | 185 |

$C_{70}$ Value - 0.64
Hardness (Rockwell H) 102

For a further evaluation of the properties of this particular composition, several specimens were prepared for staining tests. Each specimen was in the form of a disc, molded using a stainless steel mold having a diameter of 2.5 cm. and a thickness of 0.3 cm. The composition was pressed into the mold with glass plates lined with a celluloid matrix. After curing, each specimen disc was polished on one surface with a polishing stone, and then finished with Precise polishing paste, a product of Lee Pharmaceuticals, for 30 seconds. The other surface was left undisturbed, retaining its smooth matrix finish. A Gardner color reading was taken of each specimen disc before conducting further tests.

The staining tests were conducted using five different stains, with distilled water used for a control. A coffee stain was prepared by mixing 3 scoops of instant coffee with 150 ml. of distilled water. Each scoop contained approximately two tablespoons of the instant coffee. A cigarette stain was prepared by boiling two cigarettes in 50 ml. of distilled water. A tea stain was prepared by boiling one tea bag in 50 ml. of distilled water. For a soft drink stain, 50 ml. of a popular cola drink were used. For a wine stain, 50 ml. of a popular red wine were used.

Specimen discs were left immersed for 5 days in each of the staining solutions respectively, and in the distilled water control, at room temperature, and also for 24 hours at 37° C. After removal from the solutions, the specimens were brushed 100 times with a nylon bristle brush with Crest toothpaste. At that point, a reading was taken on the Gardner color meter. The observations made are as follows:

Table 1A

| | Compressive Strength and Diametral Tensile | | | |
|---|---|---|---|---|
| | 1 day at 37° C. H₂O Bath | | 1 week at 37° C. H₂O Bath | |
| Specimen Number | Compressive psi | Diametral psi | Compressive psi | Diametral psi |
| 1 | 36,269.4 | 5367.6 | 35,233 | 5623.2 |
| 2 | 35,715 | 6005.6 | 35,751 | 5367.6 |
| 3 | 34,715 | 6134.4 | 34,196.8 | 6134.4 |
| 4 | 36,787.5 | 5495.4 | 35,751 | 4728.6 |
| 5 | 35,751.2 | 6006.6 | — | — |
| Average | 35,647.6 | 5802 | 35,233 | 5463.4 |

Table 1B

| Staining Test of New Coating Composition | | | |
|---|---|---|---|
| | Gardner Color Meter - E Value | | |
| Staining Agent | Matrix Surface | Polished Surface | Visual Observation (Color Change) |
| (Control) Distilled H₂O | 0.60 | 0.81 | None |
| Coffee | 1.18 | 3.52 | Moderate |
| Cigarette | 0.59 | 1.1 | Moderate |
| Pepsi Cola | 0.36 | 0.90 | Slight |
| Tea | 0.33 | 0.61 | Slight |
| Wine | 0.33 | 0.61 | Slight |

No abrasion from brushing was observed.

As a further evaluation, the coating was applied to the tooth surfaces of several patients for the corrections of a variety of conditions. Upon recall after a period of months, there was no evidence of discoloration, and no sign of wear or loss. In most cases the restoration looked virtually unchanged.

EXAMPLE 2

Four Portion Packaging; Demonstration of a Different Resin System

The same four package technique was employed as in Example 1, but with a different liquid resin system and somewhat different formulation, as follows:

Part A

| Liquid Resin Portion | Parts by Weight |
|---|---|
| 1. Blend of 60% bis/GMA with 40% triethylene glycol dimethacrylate | 100.0 |
| 2. Cyasorb UV9 ultraviolet light absorber | 0.6 |
| 3. Aerosil | 3.0 |
| Powder Portion | Parts by Weight |
| 1. Amorphous silica, treated with silane keying agent plus 1% by weight of benzoyl peroxide | 100.0 |
| 2. Ottalume 2115 | 5.0 |
| 3. Cab-O-Sil | 5.0 |

To use, appropriate amounts of these two portions are mixed together to form a readily flowable suspension in the ratio of 1.2 parts of powder to 1 part of the liquid resin.

Part B

| Liquid Resin Portion | |
|---|---|
| 1. Blend of 60% bis/GMA with 40% triethylene glycol dimethacrylate | 100.0 |
| 2. Cyasorb UV9 | 0.4 |
| 3. N,N-bis(2-hydroxyethyl)-p-toluidine | 2.0 |
| 4. Aerosil | 3.0 |
| Powder Portion | |
| 1. Amorphous silica, treated with silane keying agent plus 1% of benzoyl peroxide | 100.0 |
| 2. Ottalume 2115 | 5.0 |
| 3. Cab-O-Sil | 5.0 |

The necessary amount of dye material was added to the Part B liquid resin, to prepare several different shades.

To use Part B, appropriate amounts of the two Part B liquid and powder portions were mixed together to form a readily flowable suspension in the ratio of 1.5 parts of powder to 1 part of the liquid binder.

After suspensions were made from each of the Part A and Part B components, equal amounts of the suspensions were then mixed together to form a paint-on coating composition in accordance with the present invention. Gel and set times were observed for several specimens, and are reported in Table 2A below.

Table 2A

| Specimen No. | Gel Time (23° C.) | Set Time (23° C.) |
|---|---|---|
| 1 | 115 secs. | 200 secs. |
| 2 | 100 secs. | 190 secs. |
| 3 | 105 secs. | 185 secs. |
| 4 | 112 secs. | 190 secs. |
| 5 | 108 secs. | 185 secs. |

Specimen discs were prepared, representing different shades, and the specimens were exposed under the sunlamp overnight. There was very slight discoloration after the exposure.

Physical tests taken on the specimens produced the results reported in Table 2B, which are compared with a test of a specimen prepared from a composition prepared in accordance with the pending patent application previously referred to, Ser. No. 751,517, filed Dec. 16, 1976. The results are reported in Table 2B below.

Table 2B

| | Physical Tests | | | | |
|---|---|---|---|---|---|
| Material | Gel Time 23° C. | Set Time 23° C. | $C_{70}$ Value | Rockwell H Hardness | Color Stability |
| Specimen of this example | 112 secs. | 190 secs. | 0.51 | 100 | Excellent |
| Specimen prepared according to Ser. No. 751,517 | 80 secs. | 120 secs. | 0.65 | 94–96 | Excellent |

Individual jars filled with the liquid and powder portions of both Parts A and B above were stored under two different storage conditions, namely, in a 37° C. environmental chamber, and at room temperature. The contents of these jars were tested every week for activity, by preparing into a paste just prior to testing. The results observed are reported in Table 2C below.

Table 2C

Shelf-Life (Storage) Test

| Approximate Time Checked | Room Temperature Storage Gel Time | Room Temperature Storage Set Time | 37° C. Environmental Chamber Storage Gel Time | 37° C. Environmental Chamber Storage Set Time |
|---|---|---|---|---|
| INITIAL | 112 sec. (23° C.) | 190 sec. (23° C.) | | |
| 5 days | 110 sec. (25° C.) | 198 sec. (25° C.) | 114 sec. (25° C.) | 195 sec. (25° C.) |
| 13 days | 114 sec. (23° C.) | 196 sec. (23° C.) | 112 sec. (23° C.) | 189 sec. (23° C.) |
| 22 days | 109 sec. (23° C.) | 188 sec. (23° C.) | 110 sec. (23° C.) 185 sec. (23° C.) | |
| 31 days | 101 sec. (25° C.) | 172 sec. (25° C.) | 108 sec. (25° C.) | 178 sec. (25° C.) |
| 48 days | 104 sec. (25° C.) | 170 sec. (25° C.) | 103 sec. (25° C.) | 168 sec. (25° C.) |
| 54 days | 105 sec. (25° C.) | 175 sec. (25° C.) | 112 sec. (25° C.) | 178 sec. (25° C.) |

Coatings prepared from the material of this example closely matched the translucency of tooth enamel. The $C_{70}$ value of human tooth enamel falls in the range from 0.21 to 0.55, depending on the kind of tooth and the plane of section. The shade of the coating prepared from the Example 2 composition depends upon the dyes employed. A light shade can be produced with a $C_{70}$ value of 0.51, and a darker shade at a value of 0.52.

When employed as a restorative coating for tooth defects, the composition of this example produces an enamel coating that has a significant effect in the restoration and prevention of enamel defects. The cured material produces a high quality restorative.

The stability against discoloration and polymerization of the composition of Example 2 were considered to be a substantial improvement over those of Example 1.

A more preferred formulation and packaging approach are described in the following example.

EXAMPLE 3

Two Portion Packaging

This example describes preferred embodiments of the invention, in each of which there are only two portions, each separately packaged, namely, a liquid resin portion and a powder portion. To accommodate different shades, the liquid resin portion may be supplied in several separate packages, each having the same composition, but each incorporating a different dye or different amount of dye, for the production of different shades.

One suitable binder formulation is as follows:

| Liquid Resin Portion | Parts by Weight |
|---|---|
| 1. Bis-GMA | 40.0 |
| 2. 2,2-bis[4'(2''-methacryloyloethoxy)-phenyl]-propane (EBA) | 40.0 |
| 3. triethylene glycol dimethacrylate | 20.0 |
| 4. Cyasorb UV 9 ultraviolet light absorber | 0.5 |
| 5. N,N-bis(2-hydroxyethyl)-p-toluidine | 0.75 |
| 6. 2-tertiary butyl-4-hydroxytolunene | 0.06 |
| Powder Package | |
| 1. barium borosilicate glass treated with silane keying agent | 100.0 |
| 2. benzoyl peroxide | 0.6 |
| 3. Ottalume 2115 | 5.0 |

Appropriate dye materials may be added to the liquid resin portion for the production of different shades, as desired.

To prepare a coating composition, the powder and liquid are mixed, preferably at a powder to liquid ratio of 2.3 to 1. An opaquing agent may be added during mixing, if desired. After the materials have been thoroughly mixed, a readily flowable mix is produced that is easily applied to a tooth surface with a spatula.

Samples of the coating composition prepared in this manner were subjected to tests, and the following results were observed:

| Sample No. | Gel Time in Seconds at 22.5° C. | Set Time in Seconds at 22.5° C. |
|---|---|---|
| 1 | 92 | 185 |
| 2 | 96 | 180 |
| 3 | 90 | 172 |

The $C_{70}$ value depended upon the shade of the coating. A very light shade was observed to have a $C_{70}$ value of 0.72, whereas a relatively dark, brown shade had a $C_{70}$ value of 0.81. The Rockwell hardness observed was 107.

Five specimens were prepared for physical tests, with the results tabulated below in Table 3A:

Table 3A

Compressive Strength and Diametral Tensile Strength

| Sample No. | 1 day at 37° C. $H_2O$ bath Compressive lbs. | 1 day at 37° C. $H_2O$ bath Compressive psi | 1 day at 37° C. $H_2O$ bath Diametral lbs. | 1 day at 37° C. $H_2O$ bath Diametral psi | 1 week at 37° C. $H_2O$ bath Compressive lbs. | 1 week at 37° C. $H_2O$ bath Compressive psi | 1 week at 37° C. $H_2O$ bath Diametral lbs. | 1 week at 37° C. $H_2O$ bath Diametral psi |
|---|---|---|---|---|---|---|---|---|
| 1 | 810 | 41968.9 | 500 | 6390 | 800 | 41450.7 | 540 | 6901.2 |
| 2 | 770 | 39896.3 | 500 | 6390 | 770 | 39896.3 | 440 | 5623.2 |
| 3 | 850 | 44041.4 | 530 | 6773.4 | 820 | 42487 | 550 | 7029 |
| 4 | 840 | 43523.3 | 480 | 6134.4 | 870 | 45077.7 | 440 | 5623.2 |
| 5 | 820 | 42487.0 | — | — | 840 | 43523.3 | 520 | 6645.6 |
| Average | | 42383.3 | | 6421.9 | | 42487 | | 6364.3 |

When the ratio of powder to liquid was changed from 2.3 to 1, as above, to 2 to 1, the physical properties remained satisfactory but somewhat lower measurements were observed.

To evaluate color stability, specimens were left under a sunlamp overnight. Very slight discoloration was observed.

Coatings applied in accordance with this example, look good, and wear well. Staining resistance is excellent.

Another preferred liquid resin formulation is as follows:

| Ingredient | Parts by Weight |
|---|---|
| BIS-GMA | 60 |
| EBA | 20 |
| triethylene glycol dimethacrylate | 20 |
| 2-tertiary butyl 4-hydroxy toluene | 0.6 |
| Cyasorb UV9 ultraviolet light absorber | 0.5 |
| N,N-bis(2-hydroxyethyl)-p-toluidine | 0.8 |

With this liquid resin, the filler composition may be employed as above, or as in either of the preceding examples, or in accordance with the general teachings of the present invention. The filler portion must, of course, contain the necessary initiator.

EXAMPLE 4

High Translucency Compositions

Other examples of satisfactory coating compositions, prepared to have a high degree of translucency, are as follows. For convenience, these compositions are reported as mixed and ready to apply to a tooth surface.

| Component | Parts by Weight |  |  |  |  |  |  |
|---|---|---|---|---|---|---|---|
|  | 4-1 | 4-2 | 4-3 | 4-4 | 4-5 | 4-6 | 4-7 |
| 60/40 blend of BIS-GMA and triethylene glycol dimethacrylate | 128 | 118 | 50 | 50 | 50 | 50 | 100 |
| amorphous silica | 120 | 60 | — | — | — | — | 75 |
| barium glass (Raysorb T-3000) | 40 | 80 | 188 | 180 | 186 | 180 | 75 |
| Cabosil | 13 | 10 | — | — | — | — | — |
| Ottalume 2115 | 10 | 10 | 2 | 10 | 4 | 10 | 20 |
| Benzoyl Peroxide | 2 | 2 | 1.0 | 1.0 | 1.0 | 4.0 | 3.5 |
| N,N-bis(2-hydroxy-ethyl)-p-toluidine | 1.5 | 1.5 | 0.75 | 0.75 | 0.75 | 0.75 | 1.5 |
| Cyasorb UV9 ultraviolet light absorber | 0.5 | 0.5 | — | — | 0.25 | 0.25 | 0.5 |

The color stability of these formulations, as measured by a 24 hour exposure under a sunlamp, was generally good when the formulation included an ultraviolet absorber, such as UV9. Examples 4-3 and 4-4 which did not contain any UV9 ultraviolet absorber, exhibited discoloration after the color stability test that was considered not acceptable. The other compositions exhibited only very slight discoloration, apparently because of the presence of UV9. The presence of very small amounts of UV9 by weight of the binder reduces the discoloration caused by ultraviolet light, without interferring with the fluorescent properties of the coating. All of the specimens demonstrated fluorescence.

EXAMPLE 5

Two Part Packaging-Effect of Accelerator Content

This example has a liquid resin system that is somewhat similar to that of Example 3. The activator content is varied, to show its effect on gel time and cure time.

| Liquid Resin Portion | Parts by Weight |
|---|---|
| BIS/GMA | 60.0 |
| EBA | 20.0 |
| Triethylene glycol dimethacrylate | 20.0 |
| 2-tertiary butyl-4-hydroxytoluene | 0.6 |
| N,N-bis(2-hydroxyethyl)-p-toluidine | 0.7 |
| Cyasorb UV9 ultraviolet light absorber | 0.5 |
| Filler Portion | Parts by Weight |
| Amorphous silica, treated with silane keying agent | 100.0 |
| Benzoyl Peroxide | 0.6 |
| Ottalume 2115 | 5.0 |

The two portions were mixed in different ratios of powder to liquid, to demonstrate the effect on gel and set times, as follows:

| Powder/Liquid Ratio | Sample No. | At 23° C. in seconds |  |
|---|---|---|---|
|  |  | Gel Time | Set Time |
| 1.5:1 | 5-1 | 128 | 240 |
|  | 5-2 | 134 | 244 |
| 1.7:1 | 5-3 | 102 | 212 |
|  | 5-4 | 102 | 209 |

When the formulation was modified by adjusting the activator content of the liquid resin from 0.7 parts to 0.8 parts, the following observations were made:

| Powder/Liquid Ratio | Sample No. | At 23° C. in seconds |  |
|---|---|---|---|
|  |  | Gel Time | Set Time |
| 1.5:1 | 5-5 | 102 | 204 |
|  | 5-6 | 100 | 197 |
| 1.7:1 | 5-7 | 85 | 158 |
|  | 5-8 | 87 | 157 |

The first-mentioned liquid resin formulation of Example 3 is preferred, since it is less viscous and therefore is easier to dispense and mix, than the resin of this example. However, the compositions of this example make coatings that are satisfactory.

CONCLUSION

The appearance of coatings made in accordance with this invention is unusually good. The fluorescent properties in particular make them virtually indistinguishable from those of natural teeth, and luster, translucency and vitality are excellent.

When properly formulated and stored at low temperatures, coating compositions packaged as described, with the curing components kept separate until ready for use, have long shelf life. The cured coatings have high structural strength, high resistance to wear and abrasion, enhanced ability to match the natural shading and vitality of tooth structure, and high bond strength to etched tooth enamel, porcelain, and acrylic without priming, and to gold after priming.

While the invention has been disclosed herein by reference to the details of several specific embodiments thereof, it is to be understood that such disclosure is intended in an illustrative rather than in a limiting sense, and it is contemplated that various modifications in the composition of the coating compositions will readily occur to those skilled in the art that are within the spirit of the invention and within the scope of the appended claims.

What is claimed is:

1. A protective and cosmetic dental coating composition for restoring enamel defects and for repairing damaged artificial teeth including chipped acrylic or porcelain veneers, which coating is sufficiently fluid that it can be applied to a tooth surface and will flow to a feather edge, but sufficiently viscous that dripping and running do not occur, and that sets in less than ten minutes to a hard coating that is bonded to the surface to which it is applied, said coating composition consisting essentially of:

A. a liquid acrylate or substituted acrylate resin that is selected from the group consisting of:

(i), a blend comprising:
(a) from 20% to not more than 90% by weight of an aromatic or cycloaliphatic: diacrylate, dimethacrylate, polyacrylate, or polymethacrylate, and
(b) at least 10% by weight of the blend of an aliphatic tri-, di-, or mono-acrylate or methacrylate;
(ii), a homopolymerizable hydrogenated aromatic diacrylate or dimethacrylate; and
(iii), mixtures thereof wherein the total amount of aromatic or cycloaliphatic diacrylate or dimethacrylate does not exceed 90% of the liquid resin;
B. a finely divided particulate filler that is a mixture of:
(i), at least 1% and not more than 20% by weight of the filler mixture of a fluorescent inorganic metal oxide pigment, with
(ii), the balance of the filler mixture of finely divided, essentially non-fluorescent inorganic filler material, the equivalent spherical diameter of the filler mixture being in the range from 0.2 micrometers to 20 micrometers;
C. curing ingredients comprising a peroxide-type initiator and an accelerator; and
D. a small but effective amount of an ultraviolet absorber; the curing ingredients of the coating being selected and present in amounts to cause curing to occur, upon admixture of the ingredients, in from about ½ minute to about 10 minutes, the filler mixture forming from 30% to 70% by weight of the coating composition and less than 50% of its volume, the density and volume of the filler mixture being selected to maintain the consistency of the uncured coating during placement so that the uncured coating is flowable but does not run or drip, the liquid resin forming essentially the balance of the composition, the cured composition having excellent vitality and cosmetic appearance and appearing natural under ultraviolet light.

2. A dental coating composition in accordance with claim 1 wherein the filler mixture comprises from 4% to 7% by weight of a fluorescent zinc-magnesium oxide pigment, and wherein the equivalent spherical diameter of the filler mixture is about 2 micrometers.

3. A dental coating composition in accordance with claim 2 that includes up to about 10% by weight of the filler mixture of a finely divided silica of sub-micrometer particle size.

4. A coating composition in accordance with claim 26 wherein the liquid resin is a blend comprising:
(a) from about 40% to about 60% 2,2-bis[4'(3" methacryloyl-2"-hydroxy-propoxy)phenyl]propane (Bis-GMA);
(b) about 20% to 40% of 2,2-bis[4'-(2"-methacryloylethoxy)phenyl]propane (EBA); the sum of (a) and (b) not exceeding 70%; and
(c) up to 80% of triethylene glycol dimethacrylate; said percentages being based on the weight of the blend.

5. A dental coating composition in accordance with claim 4 wherein the liquid resin is a blend of:
(a) about 40% of Bis-GMA;
(b) about 40% of EBA, and
(c) about 20% of triethylene glycol dimethacrylate, said percentages being percentages by weight of the blend.

6. A dental coating composition in accordance with claim 2 wherein the liquid resin is a blend of:
(a) from 20% to 60% of Bis-GMA;
(b) from 10% to 30% of triethylene glycol dimethacrylate, and
(c) from 10% up to 60% of (methacroyl-2-hydroxypropyl)-(methacroylethyl)-tetrahydrophthalate, the percentages being percentages by weight of the liquid blend.

7. A dental coating composition in accordance with claim 2 wherein the liquid resin is a blend of:
(a) from 20% to 70% by weight of the liquid resin blend of an aromatic dimethacrylate, and
(b) as the balance of the liquid resin blend, a polyethylene glycol dimethacrylate.

8. A coating composition in accordance with claim 7 wherein the aromatic dimethacrylate is bis-GMA and the polyethylene glycol dimethacrylate is triethylene glycol dimethacrylate.

9. A coating composition in accordance with claim 8 wherein the bis-GMA forms from 50% to 70% by weight of the liquid resin blend.

10. A dental coating composition in accordance with claim 3 wherein the submicron sized silica has a particle size in the range from 4 millimicrons to 50 millimicrons.

11. A coating composition in accordance with claim 3 wherein the viscosity of the liquid resin component is 5,000 centipoises or less at 25° C.

12. A method for restoring enamel defects and for repairing damaged dental surfaces including chipped acrylic or porcelain veneers and natural enamel, comprising:
flowing over a surface to be restored or repaired an initially liquid, flowable, dental restorative protective and cosmetic composition in accordance with claim 1, to cover the surface with the applied composition with a coating that extends over and beyond the area to be restored;
smoothing the applied coating to a feather edge at its extremities and permitting the composition to harden in situ on the surface.

* * * * *